(12) United States Patent
Van Den Houdt

(10) Patent No.: US 6,910,887 B2
(45) Date of Patent: Jun. 28, 2005

(54) DEVICE FOR PERFORMING AN ENDODONTIC TREATMENT

(75) Inventor: Andreas Adrianus Lambertus Van Den Houdt, Beuningen (NL)

(73) Assignee: Megadent Endo Products, B.V., Beuningen (NL)

(*) Notice: Subject to any disclaimer, the term of this patent is extended or adjusted under 35 U.S.C. 154(b) by 42 days.

(21) Appl. No.: 10/204,636

(22) PCT Filed: Feb. 22, 2001

(86) PCT No.: PCT/NL01/00151
§ 371 (c)(1), (2), (4) Date: Feb. 5, 2003

(87) PCT Pub. No.: WO01/62174
PCT Pub. Date: Aug. 30, 2001

(65) Prior Publication Data
US 2003/0152886 A1 Aug. 14, 2003

(30) Foreign Application Priority Data
Feb. 24, 2000 (NL) .............................. 1014480

(51) Int. Cl.⁷ .............................. A61C 3/00; A61C 1/07
(52) U.S. Cl. .................. 433/32; 433/118; 433/122
(58) Field of Search .................. 433/32, 102, 118, 433/119, 120, 122, 123, 124, 224

(56) References Cited

U.S. PATENT DOCUMENTS

| | | | |
|---|---|---|---|
| 3,919,775 A | | 11/1975 | Malmin |
| 4,992,045 A | * | 2/1991 | Beisel ................ 433/32 |
| 5,133,661 A | * | 7/1992 | Euvrard .............. 433/120 |
| 5,151,030 A | | 9/1992 | Comeaux |
| 5,190,456 A | * | 3/1993 | Hasegawa ........... 433/120 |
| 5,466,158 A | * | 11/1995 | Smith, III ........... 434/317 |
| 5,704,786 A | * | 1/1998 | Quinn ................ 433/128 |
| 5,893,713 A | | 4/1999 | Garman et al. |
| 5,928,220 A | * | 7/1999 | Shimoji ............... 606/2 |
| 6,270,343 B1 | * | 8/2001 | Martin ................ 433/32 |

* cited by examiner

Primary Examiner—Cary E. O'Connor
(74) Attorney, Agent, or Firm—Young & Thompson

(57) ABSTRACT

A device for use in an endodontic treatment, for example for filling a root canal of a tooth that is empty as a consequence of the removal of the nerve, with a thermoplastic product such as gutta percha, which product is distributed in the root canal by means of heating and pressing. The device includes a housing that can be grasped by hand, a treatment element provided at one end of the housing, and a device for making the treatment element vibrate.

30 Claims, 4 Drawing Sheets

DEVICE FOR PERFORMING AN ENDODONTIC TREATMENT

CROSS REFERENCE TO RELATED APPLICATION

This is the 35 USC 371 national stage of International Application PCT/NL01/00151 filed on 22 Feb. 2001, which designated the United States of America.

FIELD OF THE INVENTION

The invention relates to the field of performing endodontic treatments. With such a treatment the contents are removed from a root canal of a tooth.

BACKGROUND OF THE INVENTION

Removal of the care contents can be necessary for various reasons. The aim of the endodontic treatment is to retain the affected tooth and to prevent the consequences which pulp disorders and pulp necrosis have on the general health of the individual. The nerve can be damaged by:

enamel defects, for example as a consequence of caries;

hereditary diseases;

acquired systemic diseases;

the effects of ageing;

non-iatrogenic trauma and iatrogenic trauma

If a nerve has been damaged it can be necessary to remove it from the root canal. It is also possible that the nerve has already died. In the latter case it is necessary to remove the infected contents of the canal in order to prevent infection of the periapical area or to enable healing of a periapical infection.

For this purpose the dentist or dental surgeon clean the root canal using a file, by means of which not only the canal contents but also the dentine at the wall of the root canal is removed. Furthermore, it is possible to shape the canal correctly so that abutment with a filling material is possible. Furthermore, during this operation the pores present in the dentine are made more easily accessible, which is advantageous for obtaining the desired abutment with the filling material to be introduced.

After the root canal has been prepared, the filling material must be sealed off. A thermoplastic natural product known as "gutta percha" is used for this purpose. This product can be applied in various ways.

First of all the gutta percha can be in stick form. The sticks are placed in the root canal as required. Using a tool with a pointed tip, the sticks are then plasticised and pressed into the canal. For this purpose the tip of said tool first has to be brought to the desired temperature in a flame. In view of the speed with which the tip cools, the temperature has to be fairly high, which, incidentally, is a significant disadvantage for such a delicate treatment in the patient's mouth.

The gutta percha can also be applied in another forms. In this case so-called "Thermafil" sticks are used which consist of a plastic core coated on the outside with gutta percha. The core has a head or grip by means of which the sticks can be manipulated.

When such sticks are used the gutta percha material is also plasticised by means of heating in an oven. However, the head has to be removed from said sticks after the latter have been placed in the root canal. This is usually effected by means of a drill. In practice, however, this treatment is found to be fairly difficult to carry out. If not handled correctly, the drill can snag the core of the gutta percha filling that has been pressed in just beforehand and is still plastic, with the consequence that the core is loosened and the filling is damaged. As a result leakage can occur and the endodontic treatment can fail.

U.S. Pat. No. 5,151,030 discloses a device for performing such an endodontic treatment. This known device comprises a housing as well as means for making the latter vibrate. An electric power source is provided in the housing for heating the tip of the treatment element.

By means of an electric motor with an imbalance it is possible to make the entire housing of the device vibrate. The treatment element, which is rigidly fixed to the housing, also starts vibrating as a result. It is claimed that the root canal can be better filled with gutta percha because the treatment element vibrates. Nevertheless, this known device has the disadvantage that it is difficult to manipulate. Since the housing vibrates, it is not easy to perform the treatment in a controlled, efficient manner.

SUMMARY OF THE INVENTION

The aim of the invention is to provide a device of the type described above which does not have this disadvantage. Said aim is achieved in that there is a vibratory unit in the housing, which vibratory unit has coupling means by means of which the treatment element is coupled to it, as well as a vibration generator.

In the device according to the invention, the treatment element is coupled directly to the vibratory unit and the vibration generator. The vibrations do not have to be transferred via the housing. As a consequence, on the one hand, a powerful vibratory movement can be transmitted to the treatment element whilst, on the other hand, the housing is less affected by vibrations.

Preferably, the device is so constructed that the vibratory unit has an opening at that end of the housing that faces towards the treatment element and is provided with coupling means at that location.

An excellent effect can obtained if the coupling means and the vibration generator are located at opposite ends of the vibratory unit.

The vibration generator can be constructed in various ways; preferably, it comprises an electric motor with an imbalance.

In order to be able to perform the desired vibrations, the vibratory unit is accommodated with play in a bore in the housing and is supported with respect to the wall of the bore by means of a flexible suspension. The suspension comprises at least one O-ring that is accommodated between the housing and the wall of the bore, and in particular two or more O-rings, one of which is positioned centrally between the ends of the vibratory unit and is relatively stiff, and another of which is positioned close to one end of the vibratory unit and is relatively flexible.

The relatively stiff O-ring acts as a tilt or rocker support for the complete vibratory unit. The relatively flexible O-ring allows greater deflections of the vibratory unit and also provides the desired damping.

The treatment unit is coupled to the housing such that it is interchangeable. This is effected by means of a snap-fit connection that is able to transmit, on the one hand, the vibrations and, on the other hand, the electric current for the resistance wire.

To this end the vibratory unit has an axial recess in which the associated end of the treatment element support is inserted, in which recess at least two snap-fit elements, such as balls, can be held under resilient pretension pressed inwards in the radial direction, and the treatment element has a peripheral groove into which said snap-fit elements are snapped when inserting the support in the recess.

The axial recess and the associated end of the support also have a non-circular shape over at least a portion of their length in order to block rotation with respect to one another.

With the device according to the invention, the tip of the treatment element can furthermore be electrically heated. This has the advantage that the tip can always be kept at the ideal temperature. It is not necessary to bring the tip to a higher temperature beforehand since any cooling can be compensated for immediately by means of suitable control of the electric current by means of which the tip of the treatment element is heated. For this purpose the housing is provided with switching and/or control means for bringing the treatment element to a preset temperature.

The shape and heating control of the treatment element, also referred to as the tip or insert, are suited to rendering the gutta percha plastic and pressing it in. As an alternative, another treatment element (spoon insert) can also be used, the shape and temperature control of which are suited to removal of the head or the grip of the "Thermafil" sticks after these have been inserted and moulded into the root canal.

The treatment element (tip or insert) can be constructed in various ways. In particular, the treatment element (tip or insert) can be provided with a resistance wire that is connected to the electrical power source. Furthermore, the treatment element has a hollow needle or tube made of metal at that end that faces away from the housing, through which hollow needle or tube the resistance wire extends.

The resistance wire, which can be made of Alumel, must not make contact with the needle or tube surrounding it. This can be achieved if the resistance wire is fixed, in any event at that end thereof that faces away from the housing, to a thickening made of another metal, for example copper, which thickening is fixed to the needle or tube close to the free tip thereof. In this respect the resistance wire can also be accommodated in a sleeve made of insulating material. Very good centring of the resistance wire in the needle or tube can be obtained if it is fixed at both ends to a thickening made of another metal, for example copper, around which thickenings the sleeve fits tightly such that the resistance wire is some distance away from the sleeve.

The needle or tube is preferably constructed with a straight section, adjoining the tip thereof, a curved section and a straight section located in the support, in which straight section adjoining the tip the resistance wire and sleeve extend.

The support has electrical contacts for connecting the needle or tube and the resistance wire to the source of electricity.

As already mentioned, the filling material must be pressed in in a reliable manner, after it has been plasticised by heating, such that the root canal is completely filled.

In practice, to date this has had to be achieved by pressing in the filling material as well as possible using the treatment element. However, it remains difficult to obtain the desired sealing of the filling material and in this respect also the device according to the invention affords an improvement because the housing is provided with means for making the treatment element (tip or insert) vibrate.

The combined effect of heating, pressing in and vibrating the filling material has the result that this material is able to penetrate well into the root canal and the pores of the canal wall, even in locations which are not readily accessible.

BRIEF DESCRIPTION OF THE DRAWINGS

The invention will be explained in more detail below with reference to an illustrative embodiment shown in the figures.

DETAILED DESCRIPTION OF THE INVENTION

Figure 1:
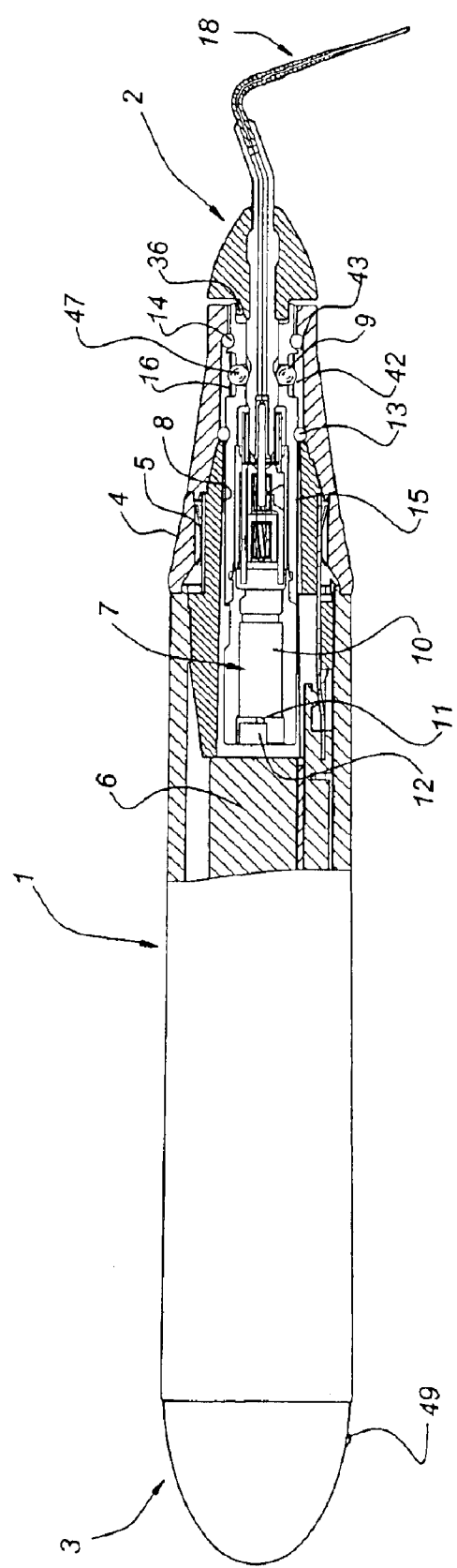
FIG. 1 shows a longitudinal section trough the device according to the invention.

The longitudinal section of the device according to the invention for carrying out a dental root canal treatment which is shown in FIG. 1 has a housing 1 that can be grasped by hand. A treatment element 2 is accommodated at the one end of the housing, whilst there is a removable cap 3 at the other end of the housing. A complete flexible ring 4, beneath which a switch 5 is located, is fitted on the housing. The switch 5 can be operated to activate the treatment element 2 by exerting pressure on the flexible ring 4. The switch may be made up of two contact layers between which resilient spacer elements are located, such that when a pressure is exerted, the contact layers are brought into contact with one another, with compression of the spacer elements.

A set of batteries 6, as well at electronic control means which are not indicated in more detail, is accommodated in the interior space of the housing 1. Said set of batteries can be charged via the supply contacts 49.

The housing 1 furthermore contains a vibratory unit, indicated in its entirety by 7, which is accommodated with play in the bore 8. The vibratory unit consists of an electric motor 10, on the driven shaft 11 of which an eccentrically positioned weight 12 or imbalance is provided.

The vibratory unit is suspended in the housing 1 by means of a relatively stiff O-ring 13 such that it can tilt. The vibratory unit 7 is damped to some extent by means of the relatively flexible O-ring 14. The electrical connection 15, which is to be described in more detail, and the mechanical snap-fit coupling 16 for the treatment element 2 are located in the vibratory unit. Said snap-fit coupling comprises a peripheral groove 42 in the support 19, as well as a number of balls 9, 47 that are accommodated in the housing 1 and can be snapped into said peripheral groove. Further O-rings can optionally be present in connection with restricting the stroke of the vibratory unit.

Figure 3:
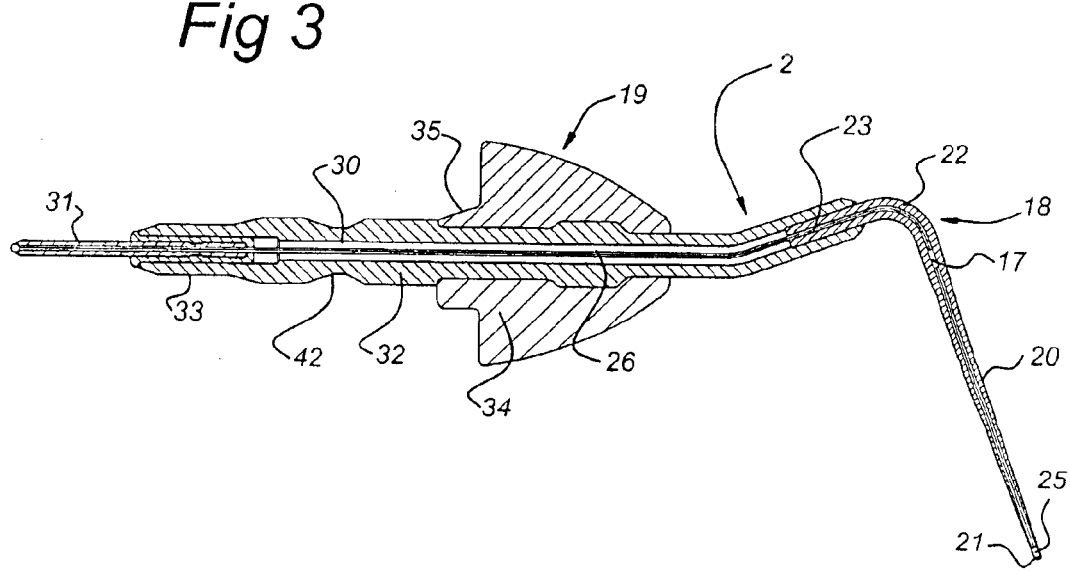
FIG. 3 shows a detail on a larger scale of the treatment element.

As shown in FIG. 3, this treatment element 2 consists of a hollow needle or tube 18 that is connected to a support 19. The hollow needle or tube 18 has a straight section 20 that adjoins the tip 21. A curved section 22 is connected to said straight section 20, which curved section is connected via a further straight section 23 to the support 19.

Figure 3A:
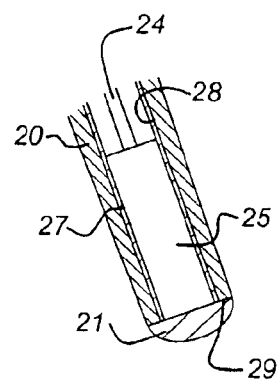
FIG. 3a shows an enlarged detail.

As is shown in FIG. 3a, a resistance wire 24, which at the outer end is fixed to a thickening 25 made of, for example, copper, is present in the straight section 20 of the hollow needle or tube 18. At the other end the resistance wire 24 is fixed to a further thickening 17, which, in turn, is connected to an insulated copper wire 26. The resistance wire 24, the thickening 25 and the thickening 17 are accommodated in an insulating sleeve 27. The whole is accommodated in the bore 28 of the straight section 20. By virtue of thickenings 17, 25 and the insulating sleeve 27, the resistance wire 24 is well insulated with respect to the wall of the bore 28. Electrically conducting materials other than copper can also be used for these components.

The copper thickening 25 is fixed, such that it is electrically conducting, to the straight section 20 by means of a weld 29 at the tip 21 of the hollow needle or tube 13.

The copper wire 26 extends through the bore 30 in the support to the central contact 31 in the form of a pin. The hollow needle or tube 18 is fixed, such that it is electrically conducting, to the metal support section 32, which, in tun, forms the other electrical contact 33.

In addition, the support 19 has a plastic support section 34 joined to the metal support section 32, which plastic support section 34 has a flattened area 35 to counteract rotation of the treatment element 2. This flattened area 35 interacts with a stop 36, as shown in FIG. 1, of the housing 1.

Figure 2:
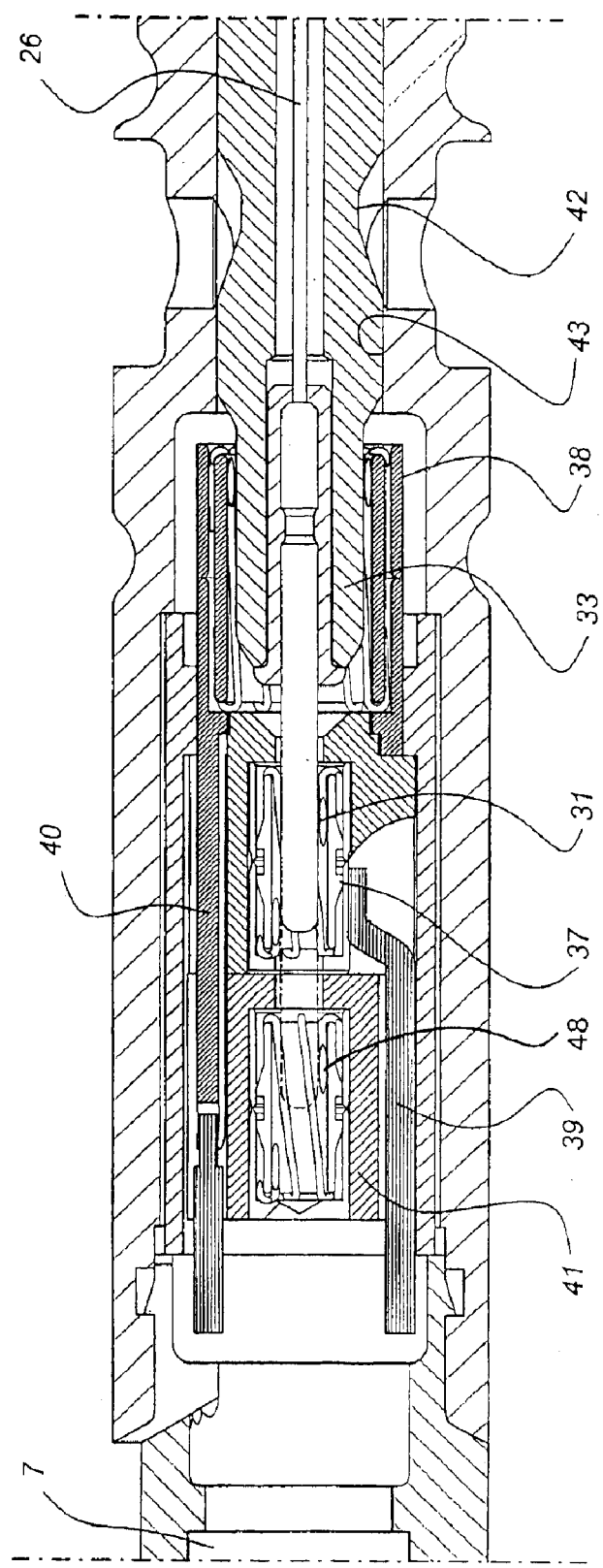
FIG. 2 shows a detail on a larger scale of the vibratory device with the electrical contacts.

As shown in FIG. 2, the insulated copper wire 26 is connected by means of the contact pin 31 to an electrical contact 37, which contains a number of resilient elements known per se.

The electrical contact 33 of the support is connected to an electrical contact 38, that likewise has a number of resilient elements known per se. These contacts are located in an axial recess 43 in which an associated end of the treatment element 2 support 19 is inserted. These contacts are connected via said electrical leads 39, 40 to the battery set 6.

There is also a third electrical contact 41 in the housing, which electrical contact 41 is offset with respect to the electrical contact 37. Said latter electrical contact 41 is suitable for detecting the type of treatment element that has an extended contact pin and is connected to the control.

If the electrical contact 37 does not detect a contact pin 48, as is the case in the situation shown by continuous lines in FIG. 2, the temperature of the heating wire can be set to, for example, 200° C. by the electronic control. In the case of positive detection of the contact pin 48, as shown by broken lines in FIG. 2, it is possible, for example, for a different temperature, such as 400° C., to be set.

During the treatment the dentist is able to generate both heating and a vibratory movement of the treatment element 2 by suitable operation of the switch 4, 5. By this means good pressing of the gutta percha into the root canal is ensured. To prevent this material sticking to the tip 21, the latter can have a diamond coating.

Figure 4:
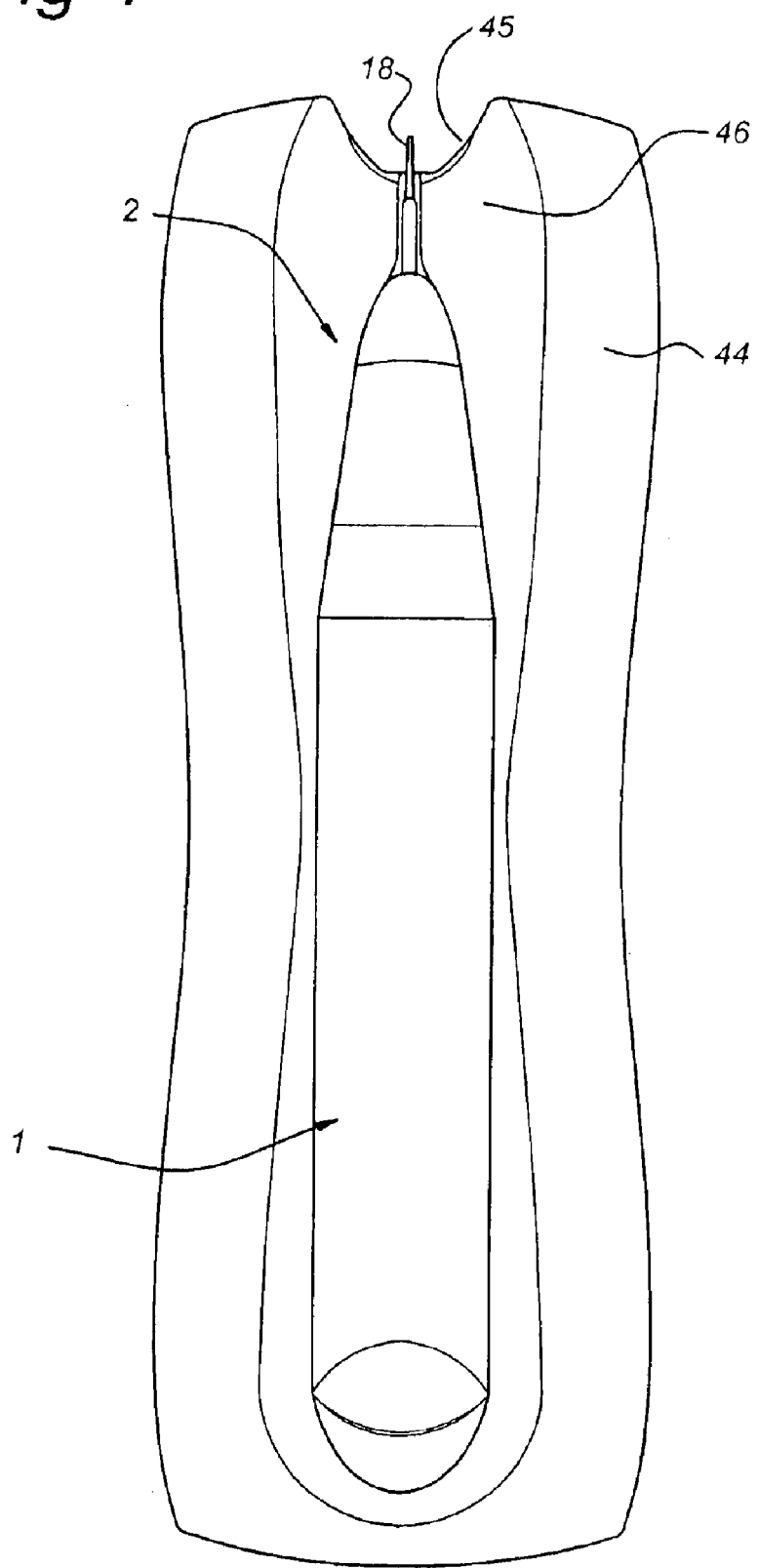
FIG. 4 shows the device accommodated in a holder.

FIG. 4 shows that the housing 1 with the treatment element 2 can be held ready in a holder 44. This holder 44 bas a longitudinal cavity 46, in which holder 1/treatment element 2 can rest. Electrical supply contacts (not shown) for charging the battery set are also present in the holder 44.

The hollow needle or tube 18 is accommodated in a well-protected manner in the recess 45 at the top edge of the holder 44.

The holder 44 can either be mounted vertically or placed on a platform.

What is claimed is:

1. Device for use in an endodontic treatment, for filling a root canal of a tooth that is empty as a consequence of the removal of the nerve, with a thermoplastic product, which is distributed in the root canal by heating and pressing, the device comprising:

a housing that can be grasped by hand;

a treatment element having a tip at one end, and provided at one end of the housing;

a vibration generator in the housing for making the treatment element vibrate;

said vibration generator being part of a vibratory unit having coupling means for coupling the treatment element thereto; and an electric power source provided in the housing for heating the tip of the treatment element.

2. The device according to claim 1, wherein the vibratory unit has an opening at that end of the housing that faces towards the treatment element and is provided with the coupling means at that location.

3. The device according to claim 1, wherein the coupling means and the vibration generator are located at opposite ends of the vibratory unit.

4. The device according to claim 1, wherein the vibration generator comprises an electric motor with an imbalance.

5. The device according to claim 1, wherein the vibratory unit is accommodated with play in a bore in the housing.

6. The device according to claim 5, wherein the vibratory unit is supported with respect to the wall of the bore by a flexible suspension.

7. The device according to claim 6, wherein the suspension comprises at least one O-ring that is accommodated between the housing and the wall of the bore.

8. Device for use in an endodontic treatment, for filling a root canal of a tooth that is empty as a consequence of the removal of the nerve, with a thermoplastic product, which is distributed in the root canal by heating and pressing, the device comprising:

a housing that can be grasped by hand;

a treatment element provided at one end of the housing;

a vibration generator in the housing for making the treatment element vibrate;

said vibration generator being part of a vibratory unit having coupling means for coupling the treatment element thereto;

said vibratory unit being supported with respect to the wall of a bore in the housing by a flexible suspension;

said flexible suspension comprising at least two O-rings, one of said O-rings being relatively stiff and accommodated between the housing and the wall of the bore and positioned centrally between ends of the vibratory unit, and the other of said O-rings being positioned close to one end of the vibratory unit and being relatively flexible.

9. The device according to claim 8, wherein the vibratory unit has an opening at that end of the housing that faces towards the treatment element and is provided with the coupling means at that location.

10. The device according to claim 8, wherein the coupling means and the vibration generator are located at opposite ends of the vibratory unit.

11. The device according to claim 8, wherein the vibration generator comprises an electric motor with an imbalance.

12. The device according to claim 8, wherein the vibratory unit is accommodated with play in a bore in the housing.

13. Device for use in an endodontic treatment, for filling a root canal of a tooth that is empty as a consequence of the removal of a nerve, with a thermoplastic product, which is distributed in the root canal by heating and pressing, the device comprising:

a housing that can be grasped by hand;

a treatment element provided at one end of the housing;

a vibration generator in the housing for making the treatment element vibrate; said vibration generator being part of a vibratory unit having an axial recess for inserting an associated end of a support for the treatment element;

the vibratory unit being provided with coupling means for coupling the treatment element thereto;

the coupling means and the treatment element forming a snap-fit connection;

the axial recess and the associated end of the support having a noncircular shape over at least a portion of their length in order to block rotation with respect to one another; and electrical contacts being located in the recess.

14. The device according to claim 13, wherein at least two snap-fit elements are held in said recess under resilient pretension pressed inwards in the radial direction, and the treatment element has a peripheral groove into which said snap-fit elements are snapped when inserting the support in the recess.

15. Device for use in an endodontic treatment, for filling a root canal of a tooth that is empty as a consequence of the removal of the nerve, with a thermoplastic product, which is distributed in the root canal by heating and pressing, the device comprising:

a housing that can be grasped by hand;

a treatment element provided at one end of the housing;

a vibration generator in the housing for making the treatment element vibrate;

said vibration generator being part of a vibratory unit having coupling means for coupling the treatment element thereto;

an electrical power source provided in the housing for heating a tip of the treatment element; and switching and/or control means for bringing the treatment element to a preset temperature.

16. Device for use in an endodontic treatment, for filling a root canal of a tooth that is empty as a consequence of the removal of the nerve, with a thermoplastic product, which is distributed in the root canal by heating and pressing, the device comprising:

a housing that can be grasped by hand;

a treatment element provided at one end of the housing;

a vibration generator in the housing for making the treatment element vibrate;

said vibration generator being part of a vibratory unit having coupling means for coupling the treatment element thereto; and an electrical power source provided in the housing for heating a tip of the treatment element;

the treatment element comprising a resistance wire that is connected to the electrical power source.

17. Device for use in an endodontic treatment, for filling a root canal of a tooth that is empty as a consequence of the removal of the nerve, with a thermoplastic product, which is distributed in the root canal by heating and pressing, the device comprising:

a housing that can be grasped by hand;

a treatment element provided at one end of the housing;

a vibration generator in the housing for making the treatment element vibrate;

said vibration generator being part of a vibratory unit having coupling means for coupling the treatment element thereto;

an electrical power source provided in the housing for heating a tip of the treatment element;

the treatment element having a hollow needle or tube made of metal at that end that faces away from the housing; and a resistance wire connected to the electrical power source and extending through the hollow needle or tube.

18. The device according to claim 17, wherein the treatment element has a support at the end facing the housing, to which support the hollow needle or tube is fixed and through which support an electrical connection for the resistance wire extends.

19. The device according to claim 17, wherein the resistance wire is fixed at that end thereof that faces away from the housing to a thickening made of another metal, which thickening is fixed to the needle or tube close to the free tip thereof.

20. The device according to claim 19, wherein the resistance wire is accommodated in a sleeve made of insulating material and is fixed at both ends to a thickening made of another metal around which the thickenings the sleeve fits tightly such that the resistance wire is some distance away from the sleeve.

21. The device according to claim 20, wherein the hollow needle or tube has a straight section adjoining the tip thereof, a curved section and a straight section located in a support of the treatment element, in which straight section adjoining the tip, the resistance wire and the sleeve extend.

22. The device according to claim 21, wherein the tip of the hollow needle or tube and the associated thickening are fixed to one another at their end faces by a laser weld.

23. The device according to claim 19, wherein the resistance wire is made of Alumel and the thickenings consist of copper wire.

24. The device according to claim 23, wherein the copper wire is insulated and extends through a curved section and through a straight section located in a support of the treatment element.

25. The device according to claim 24, wherein the treatment element and housing have electrical contacts for supplying the resistance wire with electric current.

26. In combination a device for use in an endodontic treatment, for filling a root canal of a tooth that is empty as a consequence of the removal of the nerve, with a thermoplastic product, which is distributed in the root canal by heating and pressing, the device comprising:

a housing that can be grasped by hand;

a first treatment element provided at one end of the housing;

a vibration generator in the housing for making the first treatment element vibrate;

said vibration generator being part of a vibratory unit having coupling means for coupling the first treatment element thereto, and a second treatment element having cutting or melting means;

said first and second treatment elements adapted to be fixed to the housing;

a power source provided in the housing for heating a treatment element;

the housing being provided with a pair of electrical contacts, and an electrical detection contact, such that on detection of a contact pin of a treatment element, the pair of electrical contacts is controlled to maintain a first temperature of a treatment element, and if there is no detection, the pair of electrical contacts is controlled to a second temperature of a treatment element.

27. The combination according to claim 26, wherein the contacts of the pair and the detection contact are offset with respect to one another in a longitudinal direction.

28. The combination according to claim 27, further comprising a holder in which the device can be accommodated.

29. The combination according to claim 28, wherein the holder and the housing of the device have electrical supply contacts for charging the power source.

30. The combination according to claim 28, wherein the holder has a recess at a front end in which the treatment element is accommodated.

* * * * *